(12) United States Patent
Koshima et al.

(10) Patent No.: US 7,709,678 B2
(45) Date of Patent: May 4, 2010

(54) METHOD FOR PRODUCING ASYMMETRIC ALKYL COMPOUND USING ALKALI-TREATED SOLID SUPPORT, AND ALKALI-TREATED SOLID SUPPORT USED IN THIS METHOD

(75) Inventors: Hideko Koshima, Ehime (JP); Haitao Yu, Shijiazhuang (CN)

(73) Assignee: Japan Science and Technology Agency (JP)

( * ) Notice: Subject to any disclaimer, the term of this patent is extended or adjusted under 35 U.S.C. 154(b) by 779 days.

(21) Appl. No.: 10/576,682

(22) PCT Filed: May 28, 2004

(86) PCT No.: PCT/JP2004/007393

§ 371 (c)(1),
(2), (4) Date: Jan. 16, 2007

(87) PCT Pub. No.: WO2005/040096

PCT Pub. Date: May 6, 2005

(65) Prior Publication Data

US 2007/0225157 A1 Sep. 27, 2007

(30) Foreign Application Priority Data

Oct. 24, 2003 (JP) .............................. 2003-364982

(51) Int. Cl.
*C07C 229/00* (2006.01)
*C07C 211/00* (2006.01)
(52) U.S. Cl. ...................................... 560/155; 564/291
(58) Field of Classification Search ........................ None
See application file for complete search history.

(56) References Cited

U.S. PATENT DOCUMENTS

2002/0103374 A1  8/2002  Maruoka

FOREIGN PATENT DOCUMENTS

JP  2001-48866  2/2001

OTHER PUBLICATIONS

Takahashi et al., Tetrahedron Letters 41 (2000) 8339-8342.*
Takahashi et al., J. Am. Chem. Soc. 1999, 121, 6519-6520.*
Martin J. O'Donnell et al. A new catalyst species for enantioselective alkylation by phase-transfer catalysis, Tetrahedron, vol. 50, Issue 15, pp. 4507-4518, Apr. 11, 1994.
Barry Lygo et al. "A New Class of Asymmetric Phase-Transfer Catalysts Derived From Cinchona Alkaloids—Application in the Enantioselective Synthesis of α-Amino Acids", Tetrahedron Letters, vol. 38, No. 49, pp. 8595-8598, 1997.
Adam Nelson "Asymmetric Phase-Transfer Catalysis" Agnew. Chem. Int. Ed., 38, No. 11, pp. 1583-1585, 1999.
Hyeung-geun Park et al "Highly Enantioselective and Practical Cinchona-Derived Phase-Transfer Catalysts for the Synthesis of α-Amino Acids", Agnew. Chem. Int. Ed., 41, No. 16, pp. 3036-3038, 2002.
Takashi Ooi et al., "Design of N-Spiro C2-Symmetric Chiral Quaternary Ammonium Bromides as Novel Chiral Phase-Transfer Catalysts: Synthesis and Application to Practical Asymmetric Synthesis of α-Amino Acids" , J. Am. Chem. Soc., 125, pp. 5139-5151, 2003.
Haitao Yu et al., "Alkylation of Glycine Imine Ester by Column Method", The Chemical Society of Japan 85$^{th}$ Spring Meeting 3C3-14, Mar. 28, 2005.
Haitao YU et al., "A convenient method for asymmetric alkylation of glycine imine esters using solid supports", Tetrahedron Letters 44:9209-11 (2003).
Haitao YU et al., "Asymmetric alkylation of glycine imine esters using solid supports preloaded with base", Tetrahedron 60:8405-10 (2004).
Ooi, Takashi et al., "Molecular Degisn of a C2-Symmetric Chiral Phase-Transfer Catalyst for Practical Asymmetric Synthesis of .alpha.-Amino Acids" Journal of the American Chemical Society, 121(27), 6519-6520 CODEN: JACSAT; ISSN: 0002-7863, 1999, XP002941730.
Ooi, Takashi et al., "Facile synthesis of L-Dopa tert-butyl ester by catalytic enantioselective phase-transfer alkylation", Tetrahedron Letters, 41(43), 8339-8342 CODEN: TELEAY; ISSN: 0040-4039, 2000, XP004234117.
Ooi, Takashi et al., "Practical catalytic enantioselective synthesis of .alpha.,.alpha.-dialkyl-.alpha.-amino acids by chiral phase0transfer catalysis" Journal of the American Chemical Society, 122(21), 5228-5229 CODEN: JACSAT; ISSN: 002-7863, 2000, XP002941729.

(Continued)

*Primary Examiner*—Karl J Puttlitz
(74) *Attorney, Agent, or Firm*—Sheridan Ross P.C.

(57) ABSTRACT

An asymmetric alkyl compound producing method of the present invention includes a synthesizing step of carrying out an asymmetric synthesis reaction by mixing (i) a reaction solution containing a glycine imine ester, an alkyl halide, and an asymmetric catalyst having a catalytic action which causes the asymmetric synthesis reaction to proceed with (ii) an alkali-treated solid support obtained by treating with an alkaline substance a solid support made of an inorganic compound. By placing this mixture at room temperature, the asymmetric alkylation occurs between the glycine imine ester and the alkyl halide which are catalyzed by the asymmetric catalyst in an alkali-treated solid support contained in the mixture, and the asymmetric alkylation is completed in about 1 hour. Thus, a highly optically pure asymmetric alkyl compound can be obtained in high yield. Therefore, it is possible to provide the asymmetric alkyl compound producing method which does not require the agitation of the solvent, completes the asymmetric alkylation efficiently and stably in a short time, and synthesizes a highly optically pure asymmetric alkyl compound in high yield.

24 Claims, No Drawings

OTHER PUBLICATIONS

Ooi, Takashi et al., "Conformationally flexible, chiral quaternary ammonium bromides for asymmetric phase-transfer catalysis" Angewandte Chemie, International Edition, 41(9), 1551-1554 CODEN: ACIEF5, ISSN: 1433-7851, 2002, XP001123951.

Thierry, Baptiste et al., "Solution- and solid-phase approaches in asymmetric phase-transfer catalysis by cinchona alkaloid derivatives", Synthesis, (11), 1742-1746 CODEN: SYNTBF; ISSN: 0039-7881, 2001, XP002437535.

Supplementary European Search Report for corresponding European Patent Application No. EP 04745429.3, mailed Jun. 26, 2007.

* cited by examiner

METHOD FOR PRODUCING ASYMMETRIC ALKYL COMPOUND USING ALKALI-TREATED SOLID SUPPORT, AND ALKALI-TREATED SOLID SUPPORT USED IN THIS METHOD

TECHNICAL FIELD

The present invention relates to a method for producing an asymmetric alkyl compound which can be used as a source of an optically active amino acid, and especially to a method for producing the asymmetric alkyl compound by using an asymmetric catalyst in an alkali-treated solid support.

BACKGROUND ART

An optically active amino acid is widely used as a material of food products and a synthetic intermediate of medical products. For example, an L-body optically active amino acid is an important source of nutrient for animals, while a D-body optically active amino acid that is an optical isomer of the L-body optically active amino acid increases in necessity and importance as a source of medical products in recent years. Therefore, establishing a method for selectively synthesizing these L-body and D-body optically active amino acids is an industrially important issue.

As a method for eventually obtaining the optically active amino acid, there is a method for synthesizing an asymmetric alkyl compound by an asymmetric alkylation of a glycine imine ester. This synthetic method is used so often in recent years, and uses a phase-transfer catalyst (phase-transfer catalysis). In this synthetic method, two kinds of solvents which do not blend with each other are used, and the phase-transfer catalyst moves between these solutions. Thus, the asymmetric alkylation of the glycine imine ester is repeatedly carried out, and the asymmetric alkyl compound is synthesized continuously. The following will explain the synthetic method in detail by showing an example of obtaining optically pure p-(4-chlorophenyl) alanine as an end product. In this example, a cinchonine base that is one of natural alkaloids is used as the asymmetric catalyst, and the glycine imine ester and an alkyl halide are used as the sources.

In this synthetic method, water and dichloroethane are used as solvents which do not blend with each other. Here, NaOH is dissolved in the water phase, and the cinchonine base, the glycine imine ester, and the alkyl halide are dissolved in the dichloroethane phase. Next, these solvents are agitated so as to mix together. Then, in the dichloroethane phase, the cinchonine base acts as the asymmetric catalyst, and the asymmetric alkylation occurs between the glycine imine ester and the alkyl halide.

By this asymmetric alkylation, a highly optically pure asymmetric alkyl compound is produced from the glycine imine ester and the alkyl halide. Moreover, here, the cinchonine base is converted into a conjugate acid, becomes ionic, and then moves to the water phase. Then, by NaOH dissolved in the water phase, the ionic cinchonine is again converted into a neutral cinchonine base, and returns to the dichloroethane phase. The cinchonine base in the dichloroethane phase catalyzes the asymmetric alkylation.

By repeatedly carrying out a series of alkylation steps, an asymmetric alkyl compound synthesizing method of the conventional technology can synthesize the highly optically pure asymmetric alkyl compound in high yield. Here, the produced asymmetric alkyl compound contains an (R)-body optical isomer(s) and an (S)-body optical isomer(s). In the produced asymmetric alkyl compound, the (R)-body optical isomer is larger in amount than the (S)-body optical isomer or the (S)-body optical isomer is larger in amount than the (R)-body optical isomer. Therefore, the optically pure asymmetric alkyl compound can be separated by recrystallization from the asymmetric alkyl compound. Thus, the optically pure asymmetric alkyl compound can be obtained. Further, the optically pure asymmetric alkyl compound thus obtained is, for example, hydrolyzed so that any amino acid can be synthesized.

The asymmetric alkyl compound synthesizing method as above is disclosed in, for example, O'Donnell, M. J.; Wu, S.; Hoffman, C. Tetrahedron, Vol 50, 4507-4518, 1994 (hereinafter referred to as "Conventional Example 1") and Lygo, B.; Wainwright, P. G. Tetrahedron Lett., Vol 38, 8595-8598, 1997 (hereinafter referred to as "Conventional Example 2").

However, the conventional technologies disclosed in Conventional Examples 1 and 2 cannot synthesize the asymmetric alkyl compound in a short time efficiently.

For example, in the conventional methods, the asymmetric alkylation is carried out at an interphase (interface) between the dichloroethane phase and the water phase. Therefore, it is necessary to increase the area of the interface as much as possible so that the asymmetric alkylation is efficiently carried out. To increase the area of the interface as much as possible, the solvents of water and dichloroethane needs to be agitated continuously and vigorously. As a result, the asymmetric alkylation is carried out unstably because of the unevenness of the agitation. Moreover, to obtain a product in high yield, long agitation (longer than 20 hours) is necessary. Further, when extracting the product obtained by the asymmetric alkylation, it is necessary to use a large amount of solvent different from the solvent used for the asymmetric alkylation. Therefore, an operation of extracting the product is troublesome.

DISCLOSURE OF INVENTION

The present invention was made to solve the above-described conventional problems, and an object of the present invention is to provide (i) a method for producing asymmetric alkyl compound which method (a) does not require long and vigorous agitation of a solvent (the long and vigorous agitation is required in the conventional technologies), (b) can complete an asymmetric alkylation in a short time, efficiently, and stably, and (c) can produce a highly pure asymmetric alkyl compound in high yield, and (ii) an alkali-treated solid support used in this method.

To solve the above-described problems, an asymmetric alkyl compound producing method of the present invention is a producing method for producing an asymmetric alkyl compound by an asymmetric synthesis reaction between a glycine imine ester and an alkyl halide, and the method includes a synthesizing step of carrying out the asymmetric synthesis reaction by mixing (i) a reaction solution containing the glycine imine ester, the alkyl halide, and an asymmetric catalyst having a catalytic action which causes the asymmetric synthesis reaction to proceed with (ii) an alkali-treated solid support obtained by treating with an alkaline substance a solid support made of an inorganic compound.

Moreover, in the producing method of the present invention, the above-described mixing is carried out so that the reaction solution is formed as a thin film on the surface of the alkali-treated solid support.

Moreover, in the producing method of the present invention, the above-described mixing is carried out by dropping the reaction solution onto the alkali-treated solid support.

Moreover, in the producing method of the present invention, the alkali-treated solid support is a powder.

Moreover, in the producing method of the present invention, after the above-described mixing, the resulting mixture of the reaction solution and the alkali-treated solid support is dried and then is subjected to a microwave irradiation treatment.

Moreover, in the producing method of the present invention, the solid support is any one of a clay mineral and an inorganic oxide.

Moreover, in the producing method of the present invention, the inorganic oxide is any one of a metal oxide and a silicone oxide.

Moreover, in the producing method of the present invention, the solid support is any one selected from a group consisting of alumina, kaolin, kaolinite, montmorillonite, bentonite, celite, zeolite, and diatomous earth.

Moreover, in the producing method of the present invention, used as the alkaline substance for treating the solid support is an aqueous solution of an alkali compound.

Moreover, in the asymmetric alkyl compound producing method of the present invention, used as the alkali compound is a hydroxide of alkali metal or a hydroxide of alkaline earth metal.

Moreover, in the producing method of the present invention, the alkali-treated solid support is obtained by a preparation method including (i) a treating step of treating the solid support with the aqueous solution of the alkali compound, and (ii) a drying step of drying the solid support thus treated.

Moreover, in the producing method of the present invention, in the drying step, the treated solid support is subjected to the microwave irradiation treatment so as to be dried.

Moreover, in the producing method of the present invention, the alkali-treated solid support is obtained by a preparation method including (i) a treating step of treating the solid support with the aqueous solution of the alkali compound, and (ii) a wet-state step of changing the treated solid support into a wet state.

Moreover, in the producing method of the present invention, in the wet step, moisture in the treated solid support is removed so that the amount of the moisture in the treated solid support is in a range from 0.1% by weight to 50% by weight.

Moreover, in the producing method of the present invention, the asymmetric catalyst is a cinchonidine-based compound or a cinchonine-based compound.

Moreover, in the producing method of the present invention, the asymmetric catalyst is a cinchonidine-based compound or a cinchonine-based compound.

Moreover, in the producing method of the present invention, the asymmetric catalyst is cinchonine or an N-anthracenyl methyl cinchonidium chloride.

Moreover, in the producing method of the present invention, the asymmetric catalyst is an N-spiro quaternary ammonium salt.

Moreover, in the producing method of the present invention, the glycine imine ester has a structure shown by Formula (6) below, $$(R^1)_2C=N-CH_2-COO-R^2 \quad (6)$$

where each of $R^1$ and $R^2$ denotes a monovalent organic group.

Moreover, in the producing method of the present invention, the organic group denoted by $R^1$ in Formula (6) is an aromatic group having an aromatic structure.

Moreover, in the producing method of the present invention, the organic group denoted by $R^2$ in Formula (6) includes a side chain having three or more carbons.

Moreover, in the producing method of the present invention, the organic group denoted by $R^2$ is a t-butyl group (a methyl propyl group).

Moreover, in the producing method of the present invention, the glycine imine ester is an N-dimethylphenylmethylene glycine t-butyl ester.

Moreover, in the producing method of the present invention, the alkyl halide has a structure shown by the following Formula (7).

$$R^3-X \quad (7)$$

where $R^3$ denotes a monovalent organic group, and X denotes a halogen atom.

Moreover, in the producing method of the present invention, the halogen is bromine (Br), fluorine (F), iodine (I), or chlorine (Cl).

Moreover, in the producing method of the present invention, the organic group denoted by $R^3$ is an alkyl group.

Moreover, an alkali-treated solid support of the present invention is used in the synthesizing step of the producing method, and the alkali-treated solid support is obtained by (i) treating a powder of the solid support, made of the inorganic compound, with the aqueous solution of the alkali compound, and then (ii) drying the treated powder by the microwave irradiation treatment.

Moreover, an alkali-treated solid support of the present invention is used in the synthesizing step of the producing method, and the alkali-treated solid support is obtained by (i) treating a powder of the solid support, made of the inorganic compound, with the aqueous solution of the alkali compound, and then (ii) changing the treated powder into the wet state.

Moreover, an alkali-treated solid support of the present invention is used in the synthesizing step of the asymmetric alkyl compound producing method, and the alkali-treated solid support is obtained by (i) treating a powder of the solid support, made of the inorganic compound, with the aqueous solution of the alkali compound, and then (ii) removing moisture from the treated powder so that the amount of moisture in the treated powder is in a range from 0.1% by weight to 50% by weight.

Moreover, the alkali-treated solid support of the present invention is, after the synthesizing step, washed with a washing solvent and then dried or changed into the wet state, so as to be reusable.

Moreover, in the alkali-treated solid support of the present invention, the washing solvent is a solvent used for the reaction solution.

As described above, since the asymmetric alkylation is carried out in the alkali-treated solid support in the asymmetric alkyl compound producing method of the present invention, the asymmetric alkyl compound producing method of the present invention does not require the long agitation of the solvent (although the long agitation is necessary for the conventional technologies), and can produce the highly optically pure asymmetric alkyl compound in high yield in a short time (that is, several minutes to about 1 hour).

Additional objects, features, and strengths of the present invention will be made clear by the description below.

BEST MODE FOR CARRYING OUT THE INVENTION

The following will explain one embodiment of the present invention in detail. Note that the present invention is not limited to the following embodiment.

An asymmetric alkyl compound producing method of the present invention includes a synthesizing step of carrying out an asymmetric synthesis reaction by mixing (i) a reaction solution containing a glycine imine ester, an alkyl halide, and an asymmetric catalyst having a catalytic action which causes the asymmetric synthesis reaction to proceed with (ii) an alkali-treated solid support obtained by treating with an alkaline substance a solid support made of an inorganic compound. Here, the following will explain in detail (I) the alkali-treated solid support used in the present invention, (II) the reaction solution used in the present invention, and (III) a mixture of the alkali-treated solid support and the reaction solution used in the present invention.

(I) Alkali-Treated Solid Support

An alkali-treated solid support usable in the present invention can be obtained by treating with an alkaline substance a solid support made of an inorganic compound. Here, the following will explain in detail (i) the solid support usable in the present invention, (ii) an alkaline treatment with respect to the solid support, and (iii) an ultrasonic irradiation treatment and a drying treatment both of which are applicable to the alkaline treatment.

Usable Solid Support

The solid support which is subjected to the alkaline treatment in the present step may be any support as long as the support is made of an inorganic compound. The structure and composition of the support may be any structure and composition as long as the support has such a nature that alkali, such as sodium hydrate, can stick to the surface of the support. Moreover, this solid support may be a pure substance or a mixture. Specific examples of the solid support are a metal oxide, a metal fluoride, and a semiconductor (silicon, etc) oxide. These compounds may be used alone or as a mixture of two or more compounds. Examples of the mixture are a clay mineral containing the above-described compound(s), and ceramics.

More specific examples of the solid support are alumina, titanium oxide, kaolin, kaolinite, montmorillonite, bentonite, celite, zeolite, diatomous earth, etc., however the examples of the solid support are not limited to these. These compounds and minerals may be used alone or as a mixture of two or more compounds and/or minerals. Moreover, to carry out an asymmetric alkylation (will be described later) efficiently and promptly, it is preferable that the total surface area of the solid support be as large as possible. On this account, it is preferable that the solid support have, for example, a urethane-like and fine net-like structure.

Alkaline Treatment of Solid Support

A known method may be used when treating the above-described solid support with the alkaline substance. The alkaline substance used in this alkaline treatment may be any alkali compound. An example of the alkali compound is hydroxide of an alkali metal or an alkaline earth metal, however the example of the alkali compound is not limited to this.

Moreover, it is preferable that the alkali compound used here be strong alkali. With this, the alkaline treatment can be carried out securely and adequately. Examples of the strong alkali compound are lithium hydroxide, sodium hydrate, potassium hydrate, cesium hydroxide, etc., however the examples of the strong alkali compound are not limited to these.

Moreover, a treating method for realizing this alkaline treatment may be any treating method, as long as the treating method can cause alkali to consequently stick to the solid support. For example, the alkaline treatment can be carried out by spraying the solid support with the above-described vaporized alkali compound.

It is preferable that the alkaline treatment be carried out by immersing the solid support in a strong alkali aqueous solution. Here, it is preferable that the concentration of the alkali compound in the aqueous solution be in a range from 10% to 50%, and it is more preferable that the concentration of the alkali compound in the aqueous solution be in a range from 20% to 25%. If the concentration of the alkali compound in the aqueous solution is in this range, the alkaline treatment is carried out adequately with respect to the solid support. Note that a length of time of the alkaline treatment with respect to the solid support may be any length of time, however it is preferable that the length of time be 4 hours or longer so that the alkaline treatment is adequately carried out with respect to the entire solid support. By doing so, the asymmetric alkylation in the alkali-treated solid support is carried out more efficiently.

Moreover, the number of times the alkaline treatment is carried out with respect to the solid support does not have to be once, but may be more times. When carrying out the alkaline treatment by immersing the solid support in the alkali aqueous solution, the solid support is subjected to the drying treatment (will be described later) so as to be dried, and then the alkaline treatment is carried out again by immersing the solid support in the alkali aqueous solution. By repeating these steps, it becomes possible to obtain the alkali-treated solid support which can complete the asymmetric alkylation (will be described later) more efficiently and in a short time.

Ultrasonic Irradiation Treatment

When carrying out the alkaline treatment using the alkali aqueous solution as described above, it is preferable that the solid support be irradiated with ultrasound during the alkaline treatment. By this ultrasonic irradiation treatment, the alkali aqueous solution penetrates into the solid support, and thus the alkaline treatment is carried out with respect to the entire solid support. To carry out the ultrasonic irradiation, any ultrasonic generator may be used. Moreover, any frequency and intensity of the ultrasound may be used, and a length of time the solid support is irradiated with the ultrasound may be any length of time, however, for example, it is possible to carry out the alkaline treatment adequately with respect to the entire solid support by irradiating the solid support with the ultrasound of 42 kHz and 70 W for 4 hours.

Drying Treatment

When carrying out the alkaline treatment with respect to the solid support by using the alkali aqueous solution, it is necessary to vaporize moisture in the alkali-treated solid support to dry the alkali-treated solid support. Any known method may be used to vaporize the moisture in the alkali-treated solid support. For example, it is possible to vaporize the moisture in the alkali-treated solid support by placing the alkali-treated solid support in a reduced pressure environment for an appropriate length of time. Here, a known method or instrument may be used to realize this reduced pressure environment. For example, the reduced pressure environment can be realized by aspirating the air from an enclosed space in a glass instrument by using an aspirator.

Moreover, it is possible to vaporize the moisture in the alkali-treated solid support by applying with respect to the alkali-treated solid support such a heat that water molecules in the alkali-treated solid support are vaporized adequately. In this case, for example, high-temperature air, inactivate gas, or the like may be sprayed or infrared light or microwave may be emitted with respect to the alkali-treated solid support.

Among these, it is preferable that the alkali-treated solid support be irradiated with the microwave. By this microwave irradiation treatment, the water molecules penetrated into the solid support absorbs a microwave energy, and this causes a thermal motion. Thus, the water molecules are vaporized. On this account, it is possible to completely vaporize the moisture in the solid support to dry the solid support.

Here, any known method may be used to irradiate the solid support with the microwave. For example, it is possible to use a home-use microwave oven. Note that the alkali-treated solid support may be irradiated with any wattage and frequency of the microwave, and a length of time the alkali-treated solid support is irradiated with the microwave may be any length of time. These conditions may be set optimally depending on various properties, such as the shape, amount, etc. of the solid support that is a target of the microwave irradiation treatment. For example, when drying 3 grams of an aggregated alkali-treated solid support by the microwave irradiation treatment, it is possible to completely vaporize the moisture in the aggregated alkali-treated solid support by irradiating the aggregated alkali-treated solid support with the microwave of 500 W and 2.45 GHz for 15 minutes.

Wet-State Treatment

Moreover, when carrying out the alkaline treatment with respect to the solid support by using the alkali aqueous solution, the solid support may be changed into a wet state after a treating step of treating the solid support with an aqueous solution of an alkali compound. The term "wet state" denotes a state of an alkali-treated solid support from which some moisture is removed after the alkaline treatment using the alkali aqueous solution. Any known method may be used to realize this wet state. For example, it is possible to vaporize some moisture in the alkali-treated solid support by placing the alkali-treated solid support in a reduced pressure environment for an appropriate length of time. Here, a known method or instrument may be used to realize the reduced pressure environment. For example, the reduced pressure environment can be realized by aspirating the air from an enclosed space in a glass instrument by using an aspirator.

Moreover, in this wet-state treatment, it is preferable to remove the moisture in the alkali-treated solid support so that the moisture in the alkali-treated solid support is in a range from 0.1% by weight to 50% by weight. It is not preferable that the moisture of the alkali-treated solid support exceed 50% by weight since the solid support becomes a slurry and the solid support cannot be mixed with the reaction solution. Moreover, it is not preferable that the moisture of the alkali-treated solid support be 0.1% by weight or less since the asymmetric synthesis reaction becomes slow.

Further, the moisture of the alkali-treated solid support can be set accordingly in a range from 0.1% by weight to 50% by weight depending on the kind of a solvent (will be described later). For example, in the case of using a mixed solvent of toluene and trichloromethan (5:5), it is further preferable to remove the moisture in the alkali-treated solid support so that the moisture in the alkali-treated solid support be in a range from 0.5% by weight to 16% by weight, and it is especially preferable to remove the moisture in the alkali-treated solid support so that the moisture in the alkali-treated solid support be in a range from 4% by weight to 14% by weight.

Note that a length of time the alkali-treated solid support is left in a reduced pressure environment may be any length of time as long as the alkali-treated solid support changes into the wet state, and the length of time may be set optimally depending on various properties, such as the shape, amount, etc of the solid support that is a target from which some moisture is removed. For example, when removing the moisture in 3 grams of the aggregated alkali-treated solid support by a rotary evaporator so that the moisture in 3 grams of the aggregated alkali-treated solid support is in a range from 4% by weight to 14% by weight, it is possible to cause the moisture in the aggregated alkali-treated solid support to be in a range from 4% by weight to 14% by weight by placing the aggregated alkali-treated solid support in a reduced pressure environment for 15 hours to 20 hours.

Other methods for changing the alkali-treated solid support into the wet state are, for example, (i) a method for irradiating the alkali-treated solid support with the microwave in a short time and (ii) a method for adding water to the alkali-treated solid support after the alkali-treated solid support is completely dried.

Number of Times Alkali-Treated Solid Support is Used

The alkali-treated solid support thus obtained can be used for the asymmetric alkylation (will be described later) over and over again. The number of times the alkali-treated solid support is used is not especially limited. If (i) the solid support subjected to the above-described alkaline treatment is used for the asymmetric alkylation, (ii) the alkali-treated solid support is washed so that the reaction solution is removed, and then (iii) the alkali-treated solid support is dried or is changed into the wet state, the alkali-treated solid support can be used for the asymmetric alkylation over and over again (for example, about 10 times).

(II) Reaction Solution

In the asymmetric alkyl compound producing method of the present invention, used as a reaction solution to be mixed with the above-described alkali-treated solid support is a reaction solution containing the glycine imine ester, the alkyl halide, and asymmetric catalyst having a catalytic action which causes the asymmetric synthesis reaction to proceed. The following will explain in detail (i) a solvent usable for this reaction solution, (ii) the glycine imine ester, (iii) the alkyl halide, (iv) the asymmetric catalyst, and (v) a preparation method for preparing the reaction solution using (i), (ii), (iii), and (iv).

Solvent for Dissolving Asymmetric Catalyst, etc.

A solvent used for the reaction solution may be any solvent as long as the asymmetric catalyst (will be described later), the glycine imine ester, and the alkyl halide can be dissolved in the solvent. Examples of such solvent are (i) ethers, such as diethyl ether, dimethyl ether, vinyl ether, dioxane, diisopropyl ether, tetrahydrofuran, glycol dimethyl ether, etc., (ii) hydrocarbons, such as toluene, benzene, xylene, hexane, cyclohexane, etc., (iii) amides, such as dimethylformamide, dimethylacetamide, hexamethylphosphoric triamide, etc., (iv) glacial acetic acid, (v) dimethyl sulfoxide, (vi) acetonitrile, (vii) dichloromethane, (viii) trichloromethan, (ix) pyridine, etc., and a mixed solvent of two or more of the above (i) to (ix) can also be used as the above-described solvent.

When using the mixed solvent of two or more of the above (i) to (ix), examples of the mixed solvent are a mixed solvent of toluene and dichloromethane, a mixed solvent of toluene and trichloromethane, a mixed solvent of toluene and methane cyanide. Especially, when using the mixed solvent of toluene and trichloromethane as the solvent, as shown in Example 6 (will be described later), it is possible to produce the target asymmetric alkyl compound in a short time, in high yield, and in high enantiomer excess when the blend ratio of toluene to trichloromethane is 5:5.

Moreover, the solvent is not especially limited as long as the solvent is a liquid, and the solvent may be a slurry that is a suspension in which solid particles are dispersed.

Asymmetric Catalyst

The asymmetric catalyst contained in the reaction solution, that is, the asymmetric catalyst dissolved in a solvent used for the reaction solution may be any asymmetric catalyst as long as the asymmetric catalyst has the catalytic action which causes the asymmetric synthesis reaction to proceed. Further, the asymmetric catalyst dissolved in a solvent used for the reaction solution may be any catalyst as long as the catalyst has a property of advancing the asymmetric alkylation between the glycine imine ester and the alkyl halide. Examples of such asymmetric catalyst are binaphthol, rhodium complex, molybdenum complex, cinchonine and cinchonidine that are natural alkaloids, and an N-spiro quaternary ammonium salt, however the examples of the asymmetric catalyst are not limited to these.

Especially, it is preferable that the asymmetric catalyst be a cinchonidine-based compound or a cinchonine-based compound. The term "cinchonidine-based compound" means a compound having a chemical structure of cinchonidine, and the term "cinchonine-based compound" means a compound having a chemical structure of cinchonine.

Moreover, the above-described asymmetric catalyst may be combined with some sort of residue to obtain a salt as the phase-transfer catalyst. For example, in the present invention, it is possible to use as the asymmetric catalyst (i) an N-anthracenyl methyl cinchonidium chloride (HCD-ANT) obtained by combining cinchonidine with anthracene, (ii) HCD-OH obtained by combining naphthalene with two cinchonidines, (iii) HCD-allyl obtained by replacing an OH group of HCD-OH with an allyl group, or (iv) HCN—OH obtained by combining naphthalene with two cinchonines. Note that the term "HCD" means the cinchonidine-based compound, and the term "HCN" means the cinchonine-based compound. HCD-ANT, HCD-OH, HCD-allyl, and HCN—OH described above are respectively shown below by Structural Formula (1), Structural Formula (2), Structural Formula (3), and Structural Formula (4).

(1)

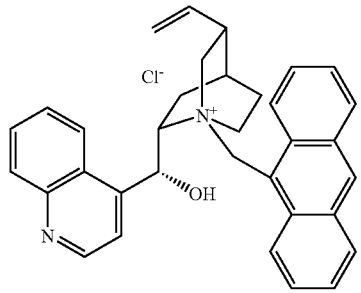

(2)

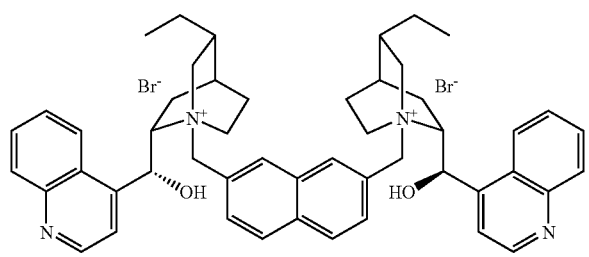

-continued (3)

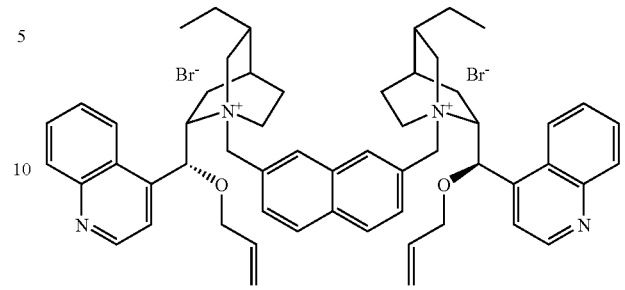

(4)

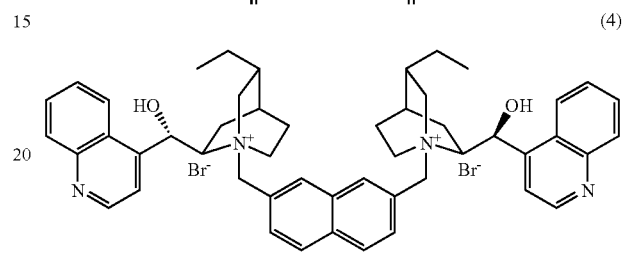

Further, an N-spiro C2-symmetric chiral quaternary ammonium bromide (hereinafter referred to as "s,s-NASB") which belongs to the N-spiro quaternary ammonium salt is shown by Structural Formula (5) below.

(5)

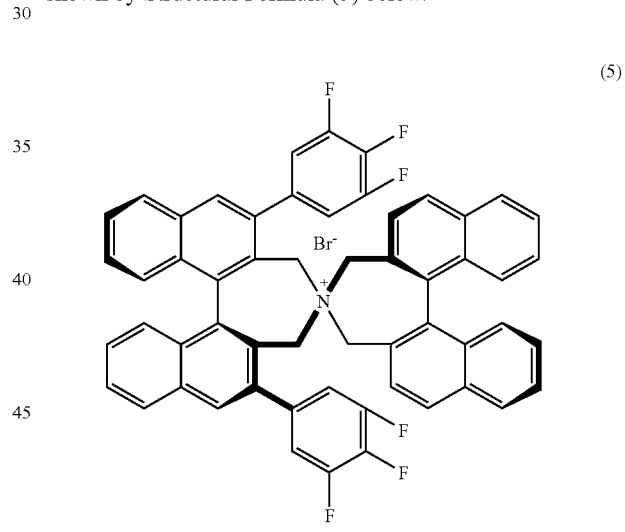

Note that an absolute configuration of the asymmetric catalyst dissolved in the solvent in the present step determines an absolute configuration (an (R) body or an (S) body) of the asymmetric alkyl compound obtained by the asymmetric synthesis in a mixing step (will be described below). For example, the asymmetric alkyl compound to be synthesized becomes an (R) body when cinchonine, HCN—OH, or S,S-NASB is used as the asymmetric phase-transfer catalyst, and becomes an (S) body when HCD-ANT, HCD-OH, or HCD-allyl is used as the asymmetric phase-transfer catalyst.

When the target asymmetric alkyl compound is the (S) body, it is preferable to use HCD-allyl as the asymmetric catalyst, as shown in Example 3 (will be described later). In this way, it is possible to produce the target asymmetric alkyl compound in a short time, in high yield, and in high enantiomer excess. When the target asymmetric alkyl compound is the (R) body, it is preferable to use HCN—OH or S,S-NASB as the asymmetric catalyst, as shown in Examples 3 and 13 (will be described later).

Note that the asymmetric catalyst of the present invention may be a commercial product or may be synthesized by a known method.

Glycine Imine Ester

It is preferable that the glycine imine ester contained in the reaction solution, that is, the glycine imine ester dissolved in a solvent used for the reaction solution is a compound shown by Chemical Formula (6) below.

$(R^1)_2C=N-CH_2-COO-R^2$ (6)

In Formula (6), each of $R^1$ and $R^2$ denotes a monovalent organic group. Moreover, it is preferable that the organic group denoted by $R^1$ be any substitutional group which can protect an amino group of the asymmetric alkyl compound to be synthesized. Examples of the organic group denoted by $R^1$ are a phenyl group, a biphenyl group, a naphthyl group, a furyl group, an alkyl group, a nitro group, and a cyano group, however the examples of the organic group denoted by $R^1$ are not limited to these. Among these, it is preferable to use the alkyl group having the aromatic structure (such as the phenyl group and the biphenyl group) since the alkyl group can protect the amino group stably.

Moreover, it is preferable that the organic group denoted by $R^2$ in Formula (6) be any substitutional group which can protect a carboxyl group of the asymmetric alkyl compound. Examples of the organic group denoted by $R^2$ are a butyl group, a propyl group, a benzyl group, and a naphthyl methyl group, however the examples of the organic group denoted by $R^2$ are not limited to these.

Moreover, it is preferable that the organic group denoted by $R^2$ be a substitutional group including a side chain having three or more carbons. This is because it is possible to more stably protect the carboxyl group of the asymmetric alkyl compound by the substitutional group whose space structure is three-dimensional. One example of the substitutional group whose space structure is three-dimensional is a tertiary substitutional group having such a structure that a carbon atom directly combined with the carboxyl group combines with three different substitutional groups. One example of the tertiary substitutional group is a t-butyl group.

Note that the glycine imine ester shown by Formula (6) may have any composition as long as the glycine imine ester is a compound which can cause the asymmetric alkylation together with the alkyl halide (will be explained later). Examples of the glycine imine ester in the present invention are an N-diphenyl methylene glycine t-butyl ester, an N-bis (4-phenyl) methylene glycine-iso-propyl ester, etc.

Moreover, the glycine imine ester used in the present invention may be a commercial product or may be synthesized by a known method.

Alkyl Halide

It is preferable that the alkyl halide contained in the reaction solution, that is, the alkyl halide dissolved in a solvent used for the reaction solution is a compound shown by Formula (7) below.

$R^3-X$ (7)

In Formula (7), $R^3$ denotes a monovalent organic group and X denotes a halogen atom. It is preferable that the organic group denoted by $R^3$ be any alkyl group. Especially, it is preferable that the organic group denoted by $R^3$ be an alkyl group which is determined (i) on the basis of the asymmetric alkyl compound synthesized in the present invention and (ii) by a substitutional group contained in an amino acid desired to be obtained eventually. That is, examples of the organic group denoted by $R^3$ are a methyl group, an ethyl group, a propyl group, a butyl group, an amyl group, a hexyl group, a benzyl group, a naphthyl methyl group, and an ester group, however the examples of the organic group denoted by $R^3$ are not limited to these.

Among these, it is preferable that organic group denoted by $R^3$ be the alkyl group (the benzyl group, the naphthyl methyl group, etc.) having the aromatic structure. Further, the organic group denoted by $R^3$ may be the alkyl group whose hydrogen is replaced with any substitutional group or a halogen. One example of the organic group denoted by $R^3$ is a parachlorobenzyl group whose hydrogen at a para position of the phenyl group is replaced with a chlorine (Cl).

Moreover, the atom denoted by X in Formula (7) may be any halogen atom. That is, the atom denoted by X may be fluorine (F), chlorine (Cl), bromine (Br), or iodine (I). To efficiently carry out the asymmetric alkylation, it is preferable that the atom denoted by X be bromine (Br). That is, it is preferable that the alkyl halide used in the present invention be alkyl bromide.

Note that the alkyl halide shown by Formula (7) may be any compound as long as the compound can cause the asymmetric alkylation together with the above-described glycine imine ester. Examples of the alkyl halide usable in the present invention are 2-(bromomethyl) naphthalene, 1-(bromomethyl)-4-chlorobenzene, bromomethylbenzene, etc.

Moreover, the alkyl halide used in the present invention may be a commercial product or may be synthesized by a known method.

Preparation of Reaction Solution

The reaction solution may be prepared by dissolving the asymmetric catalyst, the glycine imine ester, and the alkyl halide in the above-described solvent using a known method. The solvent used here may be a single kind of pure solvent, or may be a mixed solvent of a plurality of solvents which can blend with each other. There may be plural kinds of glycine imine esters and plural kinds of alkyl halides which are dissolved in the solvent, however it is preferable that there are one kind of glycine imine ester and one kind of alkyl halide in the solvent since it is possible to simplify the operation of separating and refining the asymmetric alkyl compound to be obtained.

The amount of asymmetric catalyst dissolved in the solvent may be any amount, however it is preferable that the final concentration be in a range from 0.01 M to 0.05 M. Moreover, the amount of glycine imine ester dissolved in the solvent may be any amount, however it is preferable that the final concentration be in a range from 0.1 M to 0.5 M. Further, the amount of alkyl halide dissolved in the solvent may be any amount, however it is preferable that the final concentration be in a range from 0.12 M to 0.6 M.

Here, the ratio of the glycine imine ester to the alkyl halide which are dissolved in the solvent may be any ratio, however it is preferable that the ratio of the mol concentration of the glycine imine ester to the mol concentration of the alkyl halide be 1:1. With this ratio, both the glycine imine ester and the alkyl halide can contribute to the asymmetric alkylation with no leftover glycine imine ester or alkyl halide. Moreover, the ratio of the asymmetric catalyst dissolved in the solvent to the glycine imine ester or the alkyl halide may be any ratio, however it is preferable that the ratio be in a range from 1 mol % to 20 mol %. With the ratio in this range, the asymmetric alkylation can be catalyzed effectively.

Moreover, it is preferable that the reaction solution thus prepared be used just after the preparation. This is because the dissolved asymmetric catalyst, glycine imine ester, and alkyl halide exist stably in the solvent. Note that it is possible to use the reaction solution any time by devising how to preserve the reaction solution just after the preparation. For example, the reaction solution just after the preparation may be preserved at a very low temperature (for example, −80° C. or lower).

(III) Mixing of Alkali-Treated Solid Support and Reaction Solution

The alkali-treated solid support and the reaction solution, both of which can be obtained as above, are mixed together in the present invention. By this mixing treatment, the synthesizing step of carrying out the asymmetric synthesis reaction is carried out, and in the alkali-treated solid support in the mixture, the asymmetric alkylation catalyzed by the asymmetric catalyst is carried out between the glycine imine ester and the alkyl halide. The following will explain in detail the shape and amount of the alkali-treated solid support used in this mixing treatment.

Shape and Amount of Alkali-Treated Solid Support

The shape of the alkali-treated solid support to be mixed with the reaction solution may be any shape. For example, the shape may be an aggregate, a particle, or a powder. Among these, it is preferable that the shape be such a shape that the total surface area is as large as possible. With this, it is possible to carry out the asymmetric alkylation efficiently and promptly. One example of such shape is a powder. Note that the alkali-treated solid support may be pounded finely in, for example, a mortar to obtain a powder.

Moreover, the amount of the alkali-treated solid support to be mixed with the reaction solution may also be any amount, and an appropriate amount may be suitably determined in accordance with the production amount of the target asymmetric alkyl compound.

Amount of Reaction Solution

The amount of the reaction solution to be mixed with the alkali-treated solid support may be any amount. That is, an appropriate amount may be suitably determined in accordance with the production amount of the target asymmetric alkyl compound. Here, the mixture ratio of the alkali-treated solid support to reaction solution may be any ratio. However, it is preferable to use 0.4 ml of the reaction solution when the alkali-treated solid support is 1 gram. With this, it is possible to complete the asymmetric alkylation in a short time.

It is preferable that the reaction solution be applied as thin as possible and uniformly on the surface of the alkali-treated solid support after the mixing of the alkali-treated solid support and the reaction solution in the present step. For example, it is preferable that the reaction solution be formed in the form of a thin film on the surface of the alkali-treated solid support. With this, the asymmetric alkylation in the alkali-treated solid support is carried out efficiently and promptly.

Mixing Method

Moreover, a method for mixing the alkali-treated solid support with the reaction solution may also be any known method. One example of the mixing method may be a method for dropping the reaction solution onto the powder of the alkali-treated solid support and then leaving this mixture as it is. Another example of the mixing method may be a method for continuously pouring the reaction solution into a column having any shape in which the powder of the alkali-treated solid support is placed. In the present invention, the asymmetric alkylation is carried out promptly and completed only by leaving the mixture of the alkali-treated solid support and the reaction solution at rest. Instead of leaving the mixture as it is, the mixture may be agitated by a mixer or may be shaken by a shaker.

Other Conditions

The asymmetric alkylation in the mixture may be completed in at least 1 hour at room temperature. During this asymmetric alkylation, it is preferable that the alkali-treated solid support be not dried by the evaporation of the solvent of the reaction solution contained in the mixture. This is because a considerably long time (six days or longer) becomes necessary to complete the asymmetric alkylation if the solvent evaporates. For example, the asymmetric alkylation of the mixture can be carried out at a temperature of −20° C., however in this case, a length of time necessary for completing the asymmetric alkylation becomes about five times or more a length of time necessary for completing the asymmetric alkylation at room temperature. Moreover, it is preferable that the mixture be kept under atmosphere pressure, however the mixture may be kept under any pressure as long as the solvent does not evaporate.

Microwave Irradiation Treatment

Instead of keeping the mixture under such a condition that the solvent of the reaction solution is not dried out, the asymmetric alkylation can be carried out by drying off the solvent and then carrying out the microwave irradiation treatment. With this, the asymmetric alkylation in the alkali-treated solid support is completed in about 5 minutes to 10 minutes. The wattage and frequency of the microwave used here may be any wattage and frequency, and a length of time of the microwave irradiation may be any length of time. Appropriate conditions may be suitably set in accordance with the shape, amount, etc. of the alkali-treated solid support to be subjected to the microwave irradiation treatment. For example, in the case of carrying out the microwave irradiation treatment with respect to 3 grams of the alkali-treated solid support to accelerate the asymmetric alkylation in this support, the asymmetric alkylation in this support can be completed by irradiating the alkali-treated solid support with the microwave of 500 W and 2.45 GHz for seven minutes.

Extracting Treatment

A known extracting method may be used to extract the target product, that is, the asymmetric alkyl compound from the alkali-treated solid support after the asymmetric alkylation. For example, the asymmetric alkyl compound can be extracted by washing the alkali-treated solid support with any solution capable of dissolving the asymmetric alkyl compound.

In this case, it is preferable to use the same solution as the solvent of the reaction solution used for the asymmetric alkylation. This is because it is possible to simplify an operation of refining the asymmetric alkyl compound contained in the solution used for washing. Moreover, it is preferable that the amount of the solvent used for washing be as small as possible. For example, it is preferable that the amount of the solvent used for washing be in a range from about 10 times to 50 times the reaction solution used. By washing the alkali-treated solid support with the solution the amount of which is in the above-described range, it is possible to simplify the condensation of the asymmetric alkyl compound contained in the solution.

(IV) Others

Separation and Refinement of Product

By mixing the alkali-treated solid support and the reaction solution as above, the asymmetric alkylation shown by Formula (8) below occurs, and the asymmetric alkyl compound is synthesized.

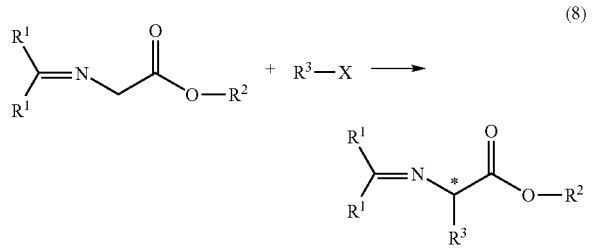

(8)

Here, $R^1$, $R^2$, and $R^3$ in Formula (8) are respectively the same as $R^1$, $R^2$, and $R^3$ in Formulas (6) and (7). Moreover, "*" denotes an asymmetric center.

The asymmetric alkyl compound synthesized by the asymmetric alkylation shown in Formula (8) has a high enantiomer excess (for example, around 80%). In other words, the asymmetric alkyl compound contains the (S) body and the (R) body, one of which is larger in amount than the other. To change this asymmetric alkyl compound into an optically pure asymmetric alkyl compound, that is, to obtain the enantiomer excess of 100%, any one of the (S)-body and the (R)-body may be separated from the asymmetric alkyl compound, and then refined.

To carry out this separation and refinement, a know separation method may be used with respect to the obtained asymmetric alkyl compound. For example, the target optical isomer can be separated from the asymmetric alkyl compound by a liquid-phase chromatography, a high performance liquid chromatography, or the like using a chiral column, etc Moreover, the target optical isomer can be separated from the obtained asymmetric alkyl compound by a naturally separating method which utilizes the fact that the (S) body and the (R) body are crystallized at different temperatures. Further, the target optical isomer may be obtained by completely degrading the nontarget optical isomer with an enzyme which degrades only one of the (S) body and the (R) body contained in the asymmetric alkyl compound. Moreover, an optically active base (kinin, strychnine, brucine, etc.) or an optically active acid (a tartaric acid, a bromo camphorsulfonic acid, etc.) may be added to the obtained asymmetric alkyl compound to obtain diastereomeric salts. In this case, these salts are separated by fractional crystallization, and then further separated by acid or alkali. In this way, the target optical isomer can be refined. It is possible to use a separation method using a synthetic polymer. This separation method utilizes the difference between the adsorptive power of the synthetic polymer with respect to the (S) body and the adsorptive power of the synthetic polymer with respect to the (R) body.

Acquisition of Optically Active Amino Acid

The asymmetric alkyl compound thus obtained has a high yield and a high enantiomer excess, so that this asymmetric alkyl compound can be used as a high quality precursor of a highly pure optically active amino acid. That is, the asymmetric alkyl compound obtained by synthesis, separation, and refinement in the steps of the present invention can be converted into various kinds of amino acids by hydrolysis. Note that a method used here for hydrolysis may be any known method.

The following will explain in more detail preferable modes of the present invention using Examples, however these Examples are just used for explaining the present invention, and the present invention is not limited to these Examples. The present invention may be altered variously by a skilled person within the scope of the present invention.

EXAMPLE 1

In Example 1, the alkali-treated solid support and the reaction solution were first obtained, and then these were mixed together, and left quietly at room temperature or at −20° C. In this way, the asymmetric alkyl compound was produced.

First, the alkali-treated solid support was prepared in the following manner. 3 grams of a support (alumina, montmorillonite K-10, kaolin) was added to 4 ml of a 25% KOH aqueous solution. This mixture was irradiated with ultrasound (42 kHz) for 4 hours. Next, with an aspirator (produced by TOKYO RIKAKIKI), moisture was removed from this mixture by filtration in a reduced pressure environment. With a 500 W home-use microwave oven (EM-LAI produced by SANYO), the solid support thus obtained was irradiated with microwave of 2.45 GHz for 15 minutes. After this microwave irradiation treatment, the alkali-treated solid support was pounded finely with a mortar. In this way, three kinds of alkali-treated solid supports (alumina/KOH, montmorillonite K-10/KOH, and kaolin/KOH) were obtained.

Next, the reaction solution was prepared in the following manner.

The reaction solution was prepared by dissolving 0.005 mmol of the asymmetric catalyst, 0.05 mmol of the glycine imine ester, and 0.063 mmol of the alkyl halide in 2 ml of dichloromethane. Here, used as the asymmetric catalyst was an N-anthracenyl methyl cinchonidium chloride, used as the glycine imine ester was an N-dimethylmethylene glycine-t-butyl ester, and used as the alkyl halide was any one of a 2-(bromomethyl) naphthalene, a 2-(bromomethyl) parachlorobenzene, and a 2-(bromomethyl) benzene.

0.5 gram of any one of the above-described three kinds of alkali-treated solid supports was added to the reaction solution thus prepared, and these were mixed together. This mixture was left quietly at room temperature for 60 minutes. Thus, the asymmetric alkylation was carried out. The status of the asymmetric alkylation was confirmed by thin layer chromatography (TLC). Note that TLC was carried out under such a condition that (i) a silica gel plate was used as a plate, and (ii) a mixed solvent of hexane, ethyl acetate, and diethyl ether (9:1:1) was used as a solvent. After the completion of the asymmetric alkylation was confirmed on the basis of the result of TLC, this reaction mixture was mixed with 5 ml of dichloroethane, and a product (asymmetric alkyl compound) was extracted from the solid support. This extracting treatment was carried out twice. The extracted product was condensed with an evaporator (produced by TOKYO RIKAKIKI).

From the reaction solution thus extracted and condensed, the target (S) body or (R) body product was separated and refined with a high performance liquid chromatography (HPLC, produced by Waters) provided with a C18 column (a length of 15 cm and a diameter of 19 mm). This HPLC carried out the separation of the product while stepwisely changing the ratio of methanol to water (v:v) from 60:40 (initial condition) to 100:0 (final condition). The enantiomer excess of the obtained product was determined by HPLC (produced by Waters) provided with a chiral column (DaicelChiralcelOD, a length of 25 cm and a diameter of 4.6 cm). The enantiomer excess was determined by pouring 1 ml, per minute, of a mixed solution of hexane and 2-propanol (99:1) to the column and measuring absorbance of 220 nm when the temperature of the column was 35° C. Moreover, the absolute configuration of a major (excessive) optical isomer ((R) or (S)) contained in the obtained product was determined on the basis of a holding time when pure (R)-body optical isomer was treated with HPLC and a holding time when pure (S)-body optical isomer was treated with HPLC.

Results are shown in Table 1 below.

TABLE 1

|   | R—Br | Support | Time (min) | Yield (%) | Enantiomer Excess (%) | Absolute Configuration |
|---|------|---------|------------|-----------|----------------------|----------------------|
| 1 | a | Kaolin | 60 | 95 | 79 | S |
| 2 | a | Mont-K10 | 60 | 93 | 75 | S |
| 3 | a | Alumina | 60 | 92 | 75 | S |
| 4 | a | Kaolin | 300 | 93 | 83 | S |
| 5 | b | Kaolin | 46 | 92 | 78 | S |
| 6 | c | Kaolin | 30 | 91 | 72 | S |

In Table 1, "R—Br" denotes the alkyl halide, each of "a", "b", and "c" denotes the kind of the substitutional group denoted by $R^3$ in Formula (7) showing the alkyl halide. Formula (9) below shows the substitutional groups corresponding to "a", "b", and "c". Moreover, "Support" in Table 1 denotes the solid support that is a target of the alkaline treatment, and "Mont-K10" denotes montmorillonite K-10.

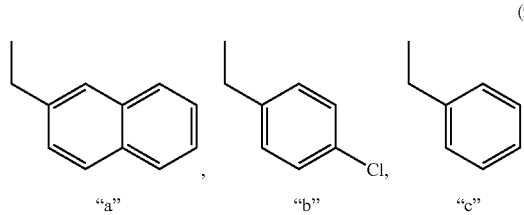

(9)

"a", "b", "c"

As shown in Table 1, in Example 1, the asymmetric alkylation was carried out under six different conditions, and a product was obtained under each condition. Here, each of the products obtained here was a product synthesized by Formula (8), and the substitutional group denoted by $R^3$ contained in the obtained product corresponds to the substitutional group denoted by "a", "b", or "c" contained in the alkyl halide used.

In the fourth condition in Table 1, a mixture of the reaction solution and kaolin/KOH was left at −20° C. to cause the asymmetric alkylation, unlike the other conditions.

According to the results shown in Table 1, the major (excessive) optical isomer contained in each of the products obtained under the six different conditions was the (S) body.

Moreover, a length of time necessary for completing the asymmetric alkylation was from 30 minutes to 60 minutes at room temperature, and 300 minutes at −20° C. Further, the yield of the product was from 93% to 95%, and the enantiomer excess was from 72% to 79%.

These results show that the asymmetric alkyl compound producing method of the present invention can produce the target asymmetric alkyl compound in a short time, in high yield, and in high enantiomer excess. Further, these results also show that the difference of the structure and kind of the alkali-treated solid support does not affect the yield of the product or the selectivity of the optical isomer.

EXAMPLE 2

The asymmetric alkyl compound was synthesized in the same way as Example 1 except that, after the reaction solution and the alkali-treated solid support were mixed together and dichloroethane that is a solvent was completely evaporated, the mixture was irradiated with the microwave of 500 W and 2.45 GHz during the asymmetric alkylation. Results are shown in Table 2 below.

TABLE 2

|   | R—Br | Support | Time (min) | Yield (%) | Enantiomer Excess (%) | Absolute Configuration |
|---|------|---------|------------|-----------|----------------------|----------------------|
| 1 | a | Kaolin | 7 | 68 | 34 | S |
| 2 | a | Mont-K10 | 8 | 58 | 32 | S |
| 3 | a | Alumina | 5 | 82 | 44 | S |
| 4 | b | Alumina | 4 | 79 | 34 | S |
| 5 | c | Alumina | 4 | 67 | 58 | S |

Here, "R—Br", etc. in Table 2 denote the same things as "R—Br", etc. in Table 1 of Example 1 denote.

As shown in Table 2, in Example 2, the asymmetric alkylation was carried out under five different conditions, and a product was obtained under each condition. Here, each of the products obtained here was a product synthesized by Formula (3), and the substitutional group denoted by $R^3$ contained in the obtained product corresponds to the substitutional group denoted by "a", "b", or "c" contained in the alkyl halide used.

Moreover, according to the results shown in Table 2, the major (excessive) optical isomer contained in each of the products obtained under five different conditions was the (S) body. Although not shown in Table 2, the major (excessive) optical isomer contained in the obtained product was the (R) body when cinchonine was used as the asymmetric catalyst.

These results show that the structure of the obtained product and the major (excessive) optical isomer do not change even if the microwave irradiation treatment is carried out with respect to the alkali-treated solid support during the asymmetric alkylation.

Meanwhile, as shown in Table 2, a length of time necessary for completing the asymmetric alkylation was from 4 minutes to 7 minutes, that is, the length of time here was reduced so as to be about one tenth of the length of time in Example 1. Moreover, the yield of the product was from 58% to 68%, and the enantiomer excess was from 32% to 58%.

These results show that, in the case of mixing the alkali-treated solid support and the reaction solution together, evaporating the solvent, and carrying out the microwave irradiation treatment, the reaction rate of the asymmetric alkylation is about 10 times higher than that in the case of not carrying out the microwave irradiation treatment.

EXAMPLE 3

Example 3 used a reaction solution prepared by dissolving 0.005 mmol of an asymmetric catalyst, 0.05 mmol of a glycine imine ester, and 0.084 mmol of an alkyl halide in 0.2 ml of dichloromethane. Here, used as the glycine imine ester was an N-dimethylmethylene glycine-t-butyl ester, used as the alkyl halide was a 2-(bromomethyl) benzene, and used as the asymmetric catalyst was any one of HCD-OH, HCD-allyl, and HCN—OH. Note that HCD-OH and HCD-allyl belong to the cinchonidine-based compounds, and HCN—OH belongs to the cinchonine-based compounds.

Moreover, used as the alkali-treated solid support was kaolin/KOH. 0.51 gram of kaolin/KOH was added to the above-described reaction solution, and these were mixed together. The mixture was left at 20° C. Thus, the asymmetric alkyl compound was synthesized, as in Example 1. Results are shown in Table 3 below.

TABLE 3

| | Asymmetric Catalyst | Time (h) | Yield (%) | Enantiomer Excess (%) | Absolute Configuration |
|---|---|---|---|---|---|
| 1 | HCD-OH | 6.5 | 86 | 84 | S |
| 2 | HCD-Allyl | 0.5 | 97 | 82 | S |
| 3 | HCN-OH | 1.0 | 97 | 81 | R |

As shown in Table 3, in Example 3, the asymmetric alkylation was carried out using three different asymmetric catalysts, and a product was obtained under each condition. As a result, a length of time necessary for completing the asymmetric alkylation was from 1 hour to 6.5 hours. Further, the yield of the product was from 86% to 97%, and the enantiomer excess was from 81% to 84%. Especially, when HCD-allyl belonging to the cinchonidine-based compounds was used as the asymmetric catalyst, the length of time necessary for completing the asymmetric alkylation, the yield of the product, and the enantiomer excess were satisfactory.

As shown in Table 3, when HCN—OH belonging to the cinchonine-based compounds was used as the asymmetric catalyst, the major (excessive) optical isomer contained in the obtained product was the (R) body.

These results show that the target asymmetric alkyl compound can be produced in a short time, in high yield, and in high enantiomer excess when HCD-allyl belonging to the cinchonidine-based compounds is used as the asymmetric catalyst.

EXAMPLE 4

Example 4 used a reaction solution prepared by dissolving 0.005 mmol of an asymmetric catalyst, 0.05 mmol of a glycine imine ester, and 0.084 mmol of an alkyl halide in 0.2 ml of dichloromethane. Here, used as the glycine imine ester was an N-dimethylmethylene glycine-t-butyl ester, used as the alkyl halide was a 2-(bromomethyl) benzene, and used as the asymmetric catalyst was HCD-allyl.

Moreover, used as the alkali-treated solid support was any one of kaolin/KOH, alumina/KOH, montmorillonite K-10/KOH, and celite/KOH. 0.51 gram of any one of the above-described four kinds of alkali-treated solid supports was added to the above-described reaction solution, and these were mixed together. The mixture was left at 20° C. Thus, the asymmetric alkyl compound was synthesized, as in Example 1. Results are shown in Table 4 below.

TABLE 4

| | Support | Time (h) | Yield (%) | Enantiomer Excess (%) | Absolute Configuration |
|---|---|---|---|---|---|
| 1 | Kaolin | 0.5 | 97 | 82 | S |
| 2 | Alumina | 3.5 | 90 | 84 | S |
| 3 | Mont-K10 | 24 | 90 | 86 | S |
| 4 | Celite | 140 | 50 | 62 | S |

As shown in Table 4, in Example 4, the asymmetric alkylation was carried out using four different supports, and a product was obtained under each condition. As a result, a length of time necessary for completing the asymmetric alkylation was from 0.5 hour to 140 hours. Further, the yield of the product was from 50% to 97%, and the enantiomer excess was from 62% to 86%. Especially, when kaolin was used as the support, the length of time necessary for completing the asymmetric alkylation, the yield of the product, and the enantiomer excess were satisfactory.

These results show that the target asymmetric alkyl compound can be produced in a short time, in high yield, and in high enantiomer excess when kaolin is used as the support.

EXAMPLE 5

Example 5 used a reaction solution prepared by dissolving 0.005 mmol of an asymmetric catalyst, 0.05 mmol of a glycine imine ester, and 0.084 mmol of an alkyl halide in 0.2 ml of dichloromethane. Here, used as the glycine imine ester was an N-dimethylmethylene glycine-t-butyl ester, used as the alkyl halide was a 2-(bromomethyl) benzene, and used as the asymmetric catalyst was HCD-allyl.

Moreover, the alkali-treated solid support was prepared by adding 3 grams of the support (kaolin) to 4 ml of an alkali aqueous solution and using the same method as in Example 1. Here, used as the alkali solution was any one of a 25% NaOH aqueous solution, a 10% KOH aqueous solution, a 15% KOH aqueous solution, a 20% KOH aqueous solution, a 25% KOH aqueous solution, and a 30% KOH aqueous solution.

0.51 gram of any one of the above-described six kinds of alkali-treated solid supports was added to the reaction solution, and these were mixed together. Thus, the asymmetric alkyl compound was synthesized, as in Example 1. Results are shown in Table 5 below.

TABLE 5

| | Alkali Aqueous Solution | Concentration (%) | Time (h) | Yield (%) | Enantiomer Excess (%) | Absolute Configuration |
|---|---|---|---|---|---|---|
| 1 | NaOH | 25 | 6.5 | 83 | 80 | S |
| 2 | KOH | 10 | 5.0 | 75 | 85 | S |
| 3 | KOH | 15 | 0.75 | 88 | 88 | S |
| 4 | KOH | 20 | 1.5 | 88 | 90 | S |
| 5 | KOH | 25 | 2.5 | 89 | 91 | S |
| 6 | KOH | 30 | 12.0 | 86 | 84 | S |
| 7 | CsOH | 25 | 1.5 | 80 | 81 | S |

As shown in Table 5, in Example 5, the asymmetric alkylation was carried out using six different alkali solutions (which were different in concentration and kind), and a product was obtained under each condition. As a result, a length of time necessary for completing the asymmetric alkylation was from 0.75 hour to 12 hours. Further, the yield of the product was from 75% to 89%, and the enantiomer excess was from 81% to 91%. Especially, when the 20% or 25% KOH solution was used as the alkali solution, the length of time necessary for completing the asymmetric alkylation, the yield of the product, and the enantiomer excess were satisfactory.

These results show that the target asymmetric alkyl compound can be produced in a short time, in high yield, and in high enantiomer excess when a 20% to 25% KOH solution is used as the alkali solution.

EXAMPLE 6

Example 6 used a reaction solution prepared by dissolving 0.005 mmol of an asymmetric catalyst, 0.05 mmol of a glycine imine ester, and 0.084 mmol of an alkyl halide in a predetermined amount of solvent. Here, used as the glycine imine ester was an N-dimethylmethylene glycine-t-butyl ester, used as the alkyl halide was a 2-(bromomethyl) benzene, and used as the asymmetric catalyst was HCD-allyl. Moreover, used as the above-described predetermined amount of solvent was any one of 0.2 ml of dichloromethane ($CH_2Cl_2$), 0.1 ml of a mixed solvent of toluene ($PhCH_3$) and dichloromethane (3:7), 0.1 ml of a mixed solvent of toluene and dichloromethane (4:6), 0.1 ml of a mixed solvent of toluene and trichloromethane (5:5), 0.15 ml of a mixed solvent of toluene and trichloromethane (6:4), 0.1 ml of a mixed solvent of toluene and trichloromethane (6:4), 0.15 ml of a mixed solvent of toluene and trichloromethane (7:3), 0.1 ml of a mixed solvent of toluene and methane cyanide ($CH_3CN$) (7:3), and 0.1 ml of a mixed solvent of toluene and methane cyanide (8:2).

Moreover, used as the alkali-treated solid support was kaolin/KOH. 0.51 gram of the alkali-treated solid support was added to the above-described reaction solution, and these were mixed together. Thus, the asymmetric alkyl compound was synthesized, as in Example 1. Results are shown in Table 6 below.

TABLE 6

| | Solvent | Amount (ml) | Time (h) | Yield (%) | Enantiomer Excess (%) | Absolute Configuration |
|---|---|---|---|---|---|---|
| 1 | $CH_2Cl_2$ | 0.20 | 0.5 | 97 | 84 | S |
| 2 | $PhCH_3$—$CH_2Cl_2$ (3:7) | 0.10 | 0.5 | 95 | 80 | S |
| 3 | $PhCH_3$—$CH_2Cl_2$ (4:6) | 0.10 | 3.0 | 95 | 80 | S |
| 4 | $PhCH_3$—$CHCl_3$ (5:5) | 0.10 | 2.0 | 89 | 91 | S |
| 5 | $PhCH_3$—$CHCl_3$ (6:4) | 0.15 | 4.0 | 99 | 92 | S |
| 6 | $PhCH_3$—$CHCl_3$ (6:4) | 0.10 | 3.0 | 96 | 90 | S |
| 7 | $PhCH_3$—$CHCl_3$ (7:3) | 0.15 | 23.0 | 71 | 93 | S |
| 8 | $PhCH_3$—$CH_3CN$ (7:3) | 0.10 | 0.67 | 96 | 72 | S |
| 9 | $PhCH_3$—$CH_3CN$ (8:2) | 0.10 | 0.83 | 97 | 72 | S |

Here, each of the fifth line and the seventh line in Table 6 show a result when the mixture of the alkali-treated solid support and the reaction solution became a slurry.

As shown in Table 6, in Example 6, the asymmetric alkylation was carried out using nine different solvents (which were different in blend ratio, kind, and/or amount), and a product was obtained under each condition. As a result, a length of time necessary for completing the asymmetric alkylation was from 0.5 hour to 23 hours. Further, the yield of the product was from 71% to 97%, and the enantiomer excess was from 84% to 91%. Especially, when used as the solvent was the mixed solvent of toluene and trichloromethane, the enantiomer excess was satisfactory. Further, when used as the solvent was 0.1 ml of the mixed solvent of toluene and trichloromethane (5:5), the length of time necessary for completing the asymmetric alkylation, the yield of the product, and the enantiomer excess were satisfactory.

These results show that the target asymmetric alkyl compound can be produced in a short time, in high yield, and in high enantiomer excess when the mixed solvent of toluene and trichloromethane is used as the solvent and especially when the mixed solvent of toluene and trichloromethane (5:5) is used as the solvent.

EXAMPLE 7

Example 7 used a reaction solution prepared by dissolving 0.005 mmol of an asymmetric catalyst, 0.05 mmol of a glycine imine ester, and 0.084 mmol of an alkyl halide in 0.2 ml of solvent. Here, used as the glycine imine ester was an N-dimethylmethylene glycine-t-butyl ester, used as the alkyl halide was a 2-(bromomethyl) benzene, and used as the asymmetric catalyst was HCN—OH belonging to the cinchonine-based compounds. Moreover, used as the solvent was any one of dichloromethane ($CH_2Cl_2$), a mixed solvent of toluene and dichloromethane (3:7), a mixed solvent of toluene and trichloromethane (5:5), and a mixed solvent of toluene and methane cyanide (8:2).

Moreover, used as the alkali-treated solid support was kaolin/KOH. 0.51 gram of the alkali-treated solid support was added to the reaction solution, and these were mixed together. Thus, the asymmetric alkyl compound was synthesized, as in Example 1. Results are shown in Table 7 below.

TABLE 7

| | Solvent | Time (h) | Yield (%) | Enantiomer Excess (%) | Absolute Configuration |
|---|---|---|---|---|---|
| 1 | $CH_2Cl_2$ | 2.0 | 97 | 81 | R |
| 2 | $PhCH_3$—$CH_2Cl_2$ (3:7) | 0.75 | 92 | 79 | R |

TABLE 7-continued

| | Solvent | Time (h) | Yield (%) | Enantiomer Excess (%) | Absolute Configuration |
|---|---|---|---|---|---|
| 3 | $PhCH_3$—$CHCl_3$ (5:5) | 2.0 | 82 | 78 | R |
| 4 | $PhCH_3$—$CH_3CN$ (8:2) | 0.33 | 91 | 57 | R |

As shown in Table 7, in Example 7, the asymmetric alkylation was carried out using (i), as the asymmetric catalyst, HCN—OH which produces the product of the (R)-body optical isomer and (ii) four different solvents (which were different in blend ratio or kind), and a product was obtained under each condition. As a result, a length of time necessary for completing the asymmetric alkylation was from 0.33 hour to 2 hours. Further, the yield of the product was from 82% to 97%, and the enantiomer excess was from 57% to 79%. Especially, when the mixed solvent of toluene and dichloromethane (3:7) was used, the time necessary for completing the asymmetric alkylation, the yield of the product, and the enantiomer excess were satisfactory.

These results show that the asymmetric alkyl compound of the target (R)-body optical isomer can be produced in a short time, in high yield, and in high enantiomer excess when the mixed solvent of toluene and dichloromethane (3:7) is used as the solvent.

EXAMPLE 8

Example 8 used a reaction solution prepared by dissolving 0.005 mmol of an asymmetric catalyst, 0.05 mmol of a glycine imine ester, and 0.084 mmol of an alkyl halide in 0.2 ml of solvent. Here, used as the glycine imine ester was an N-dimethylmethylene glycine-t-butyl ester, used as the alkyl halide was a 2-(bromomethyl) benzene, and used as the asymmetric catalyst was HCD-allyl.

Moreover, used as the alkali-treated solid support was kaolin/KOH. 0.51 gram of the alkali-treated solid support was added to the reaction solution, and these were mixed together. Then, the mixture was left quietly at 20° C., 0° C., or −30° C. Thus, the asymmetric alkyl compound was synthesized, as in Example 1. Results are shown in Table 8 below.

TABLE 8

| | Temperature (° C.) | Time (h) | Yield (%) | Enantiomer Excess (%) | Absolute Configuration |
|---|---|---|---|---|---|
| 1 | 20 | 2 | 89 | 91 | S |
| 2 | 0 | 24 | 98 | 92 | S |
| 3 | −30 | 130 | 98 | 96 | S |

As shown in Table 8, in Example 8, the asymmetric alkylation was carried out at three different reaction temperatures, and a product was obtained under each condition. As a result, a length of time necessary for completing the asymmetric alkylation was from 2 hours to 130 hours. Further, the yield of the product was from 89% to 98%, and the enantiomer excess was from 91% to 96%. Especially, when the reaction temperature was 0° C. or −30° C., the yield of the product was satisfactory. Further, when the reaction temperature was −30° C., the length of time necessary for completing the asymmetric alkylation, the yield of the product, and the enantiomer excess were satisfactory.

These results show that the target asymmetric alkyl compound can be produced in high yield and in high enantiomer excess when the reaction temperature is 0° C. or −30° C. and especially when the reaction temperature is −30° C.

EXAMPLE 9

Example 9 used a reaction solution prepared by dissolving 0.005 mmol of an asymmetric catalyst, 0.05 mmol of a glycine imine ester, and 0.084 mmol of an alkyl halide in 0.2 ml of mixed solvent of toluene and trichloromethane (5:5). Here, used as the glycine imine ester was an N-dimethylmethylene glycine-t-butyl ester, used as the alkyl halide was any one of a 2-(bromomethyl) naphthalene, a 2-(bromomethyl) parachlorobenzene, and a 2-(bromomethyl) benzene, and used as the asymmetric catalyst was HCD-allyl.

Moreover, used as the alkali-treated solid support was kaolin/KOH. 0.51 gram of the alkali-treated solid support was added to the reaction solution, and these were mixed together. Thus, the asymmetric alkyl compound was synthesized, as in Example 1. Results are shown in Table 9 below.

TABLE 9

| | R—Br | Time (h) | Yield (%) | Enantiomer Excess (%) | Absolute Configuration |
|---|---|---|---|---|---|
| 1 | a | 7.0 | 80 | 82 | S |
| 2 | b | 2.5 | 67 | 81 | S |
| 3 | c | 2.0 | 89 | 91 | S |

Here, "R—Br", etc. in Table 9 denote the same things as "R—Br", etc. in Table 1 of Example 1 deote.

As shown in Table 9, in Example 9, the asymmetric alkylation was carried out using different alkyl halides, and a product was obtained under each condition. Here, each of the products obtained here was a product synthesized by Formula (3), and the substitutional group denoted by $R^3$ contained in the obtained product corresponds to the substitutional group denoted by "a", "b", or "c" contained in the alkyl halide used.

Moreover, a length of time necessary for completing the asymmetric alkylation was from 2 hours to 7 hours. Further, the yield of the product was from 67% to 89%, and the enantiomer excess was from 81% to 91%. Especially, when 2-(bromomethyl) benzene was used as the alkyl halide, the length of time necessary for completing the asymmetric alkylation, the yield of the product, and the enantiomer excess were satisfactory.

EXAMPLE 10

Example 10 used a reaction solution prepared by dissolving 10 mol % of an asymmetric catalyst, 0.05 mmol of a glycine imine ester, and 0.084 mmol of an alkyl halide in 0.2 ml of solvent. Here, used as the glycine imine ester was an N-dimethylmethylene glycine-t-butyl ester, used as the alkyl halide was a 2-(bromomethyl) benzene, and used as the asymmetric catalyst was HCD-allyl belonging to the cinchonidine-based compounds. Moreover, used as the solvent was a mixed solvent of toluene and trichloromethane (5:5).

Moreover, used as the alkali-treated solid support was kaolin/KOH. The following will explain a preparation method of the alkali-treated solid support in Example 10. 3 grams of the support (kaolin) was added to 4 ml of a 25% KOH aqueous solution. This mixture was irradiated with ultrasound (42 kHz) for 4 hours. Next, with a rotary evaporator (produced by TOKYO RIKAKIKI), some moisture was removed from this mixture in a reduced pressure environment, at 95° C., for 2 hours. Thus, a wet state alkali-treated solid support was obtained. Here, the ratio of the moisture in the wet state alkali-treated solid support was 12%. Meanwhile, as in Example 1, the moisture was removed from the mixture with the aspirator in a reduced pressure environment, and thus a dried alkali-treated solid support was obtained.

0.51 gram of each of these two alkali-treated solid supports was added to the reaction solution, and these were mixed together. Thus, the asymmetric alkyl compound was synthesized, as in Example 1. Here, the reaction temperature here was 0° C. or 20° C. Results are shown in Table 10 below.

TABLE 10

| | Support | Reaction Temperature (° C.) | Time (h) | Yield (%) | Enantiomer Excess (%) | Absolute Configuration |
|---|---|---|---|---|---|---|
| 1 | Solid | 20 | 2 | 89 | 91 | S |
| 2 | Solid (wet) | 20 | 0.12 | 90 | 84 | S |
| 3 | Liquid-Liquid | 20 | 0.75 | 87 | 85 | S |
| 4 | Solid | 0 | 24 | 98 | 92 | S |
| 5 | Solid (wet) | 0 | 0.5 | 90 | 90 | S |
| 6 | Liquid-Liquid | 0 | 23 | 89 | 89 | S |

In Table 10, "Solid" denotes the dried alkali-treated solid support, "Solid (wet)" denotes the wet state alkali-treated solid support, "Liquid-liquid" denotes a case in which the alkali-treated solid support was not used and the asymmetric alkylation was carried out at an interphase (interface) between a solvent phase and a water phase by using a conventional method.

Table 10 shows that the structure of the obtained product and the major (excessive) optical isomer does not change even in the case of using the wet state alkali-treated solid support obtained by removing some moisture with the aspirator in a reduced pressure environment.

Moreover, as shown in Table 10, a length of time necessary for completing the asymmetric alkylation was 0.12 hour (the reaction temperature of 20° C.) when using the wet state alkali-treated solid support, that is, the length of time is reduced so as to be about one twentieth of the length of time when using the dried alkali-treated solid support. Especially, when the reaction temperature was 0° C., the length of time necessary for completing the asymmetric alkylation was 0.5 hour (the reaction temperature of 20° C.), that is, the length of time is reduced so as to be about one fiftieth of the length of time when using the dried alkali-treated solid support. Moreover, the yield of the product was 90% when the reaction temperature was 20° C. and 0° C., and the enantiomer excess was from 84% to 90%.

In Example 10, when the asymmetric alkylation was carried out at the interphase (interface) between the solvent phase and the water phase at the reaction temperature of 20° C. by using the conventional method without using the alkali-treated solid support, the length of time necessary for completing the asymmetric alkylation was shorter than the length of time when using the dried alkali-treated solid support. This occurs only when HCD-allyl was used as the asymmetric catalyst.

These results show that, when some moisture of the alkali-treated solid support is removed, the reaction rate of the asymmetric alkylation becomes about 20 times to 50 times higher than the reaction rate when the moisture of the alkali-treated solid support is completely removed.

EXAMPLE 11

Example 11 used a reaction solution prepared by dissolving 10 mol % of an asymmetric catalyst, 0.05 mmol of a glycine imine ester, and 0.084 mmol of an alkyl halide in 0.2 ml of solvent. Here, used as the glycine imine ester was an N-dimethylmethylene glycine-t-butyl ester, used as the alkyl halide was a 2-(bromomethyl) benzene, and used as the asymmetric catalyst was HCD-allyl belonging to the cinchonidine-based compounds. Moreover, used as the solvent was a mixed solvent of toluene and trichloromethane (5:5) or a mixed solvent of toluene and dichloromethane (3:7).

Moreover, used as the alkali-treated solid support was kaolin/KOH. The following will explain a preparation method of the alkali-treated solid support in Example 11. 3 grams of the support (kaolin) was added to 4 ml of a 25% KOH aqueous solution. This mixture was irradiated with ultrasound (42 kHz) for 4 hours. Next, with a rotary evaporator (produced by TOKYO RIKAKIKI), some moisture was removed from this mixture in a reduced pressure environment, at 95° C., for 2 hours. Thus, a wet state alkali-treated solid support was obtained. Here, the ratio of the moisture in the wet state alkali-treated solid support was 12%. Meanwhile, as in Example 1, the moisture was removed from the mixture with a rotary evaporator in a reduced pressure environment, and thus a dried alkali-treated solid support was obtained.

0.51 gram of each of these two alkali-treated solid supports was added to the reaction solution, and these were mixed together. Thus, the asymmetric alkyl compound was synthesized, as in Example 1. Results are shown in Table 11 below.

TABLE 11

| | Support | Time (h) | Yield (%) | Enantiomer Excess (%) | Absolute Configuration |
|---|---|---|---|---|---|
| 1 | Solid | 2 | 89 | 91 | S |
| 2 | Solid (wet) | 0.12 | 90 | 84 | S |
| 3 | Solid | 0.5 | 95 | 80 | S |
| 4 | Solid (wet) | 0.08 | 98 | 83 | S |

In Table 10, "Solid" demotes the dried alkali-treated solid support, and "Solid (wet)" denotes the wet state alkali-treated solid support.

In the first and second lines in Table 11, used as the solvent was a mixed solvent of toluene and trichloromethane (5:5). In the third and fourth lines in Table 11, used as the solvent was a mixed solvent of toluene and dichloromethane (3:7).

As shown in Table 11, when using the wet state alkali-treated solid support, a length of time necessary for completing the asymmetric alkylation was 0.12 hour, that is the length of time was reduced so as to be about one twentieth of the length of time when using the dried alkali-treated solid support. Moreover, when used as the solvent was a mixed solvent of toluene and dichloromethane (3:7), the length of time necessary for completing the asymmetric alkylation was 0.08 hours, that is, the length of time was reduced so as to be about one sixth of the length of time when using the dried alkali-treated solid support. Further, the yield of the product was from 89% to 90% and the enantiomer excess was from 83% to 84% when any one of the above solvents was used.

EXAMPLE 12

Example 12 used a reaction solution prepared by dissolving 2 mol % (0.001 mmol) or 10 mol % (0.005 mmol) of an asymmetric catalyst, 0.05 mmol of a glycine imine ester, and 0.084 mmol of an alkyl halide in a predetermined solvent. Here, used as the glycine imine ester was an N-dimethylmethylene glycine-t-butyl ester, used as the alkyl halide was a 2-(bromomethyl) benzene, and used as the asymmetric catalyst was HCD-allyl. Moreover, used as the above-described predetermined amount of solvent was any one of dichloromethane ($CH_2Cl_2$), a mixed solvent of toluene ($PhCH_3$) and dichloromethane (3:7), a mixed solvent of toluene and dichloromethane (5:5), and a mixed solvent of toluene and trichloromethan ($CHCl_3$) (5:5).

Moreover, used as the alkali-treated solid support was kaolin/KOH. The wet state alkali-treated solid support was prepared by using the same method as in Example 11. In Example 12, a length of time necessary for removing the moisture in the wet state alkali-treated solid support with a rotary evaporator in a reduced pressure environment was suitably set so that the ratio of the moisture in the wet state alkali-treated solid support can be from 0% to 18%.

0.51 gram of the alkali-treated solid support was added to the reaction solution, and these were mixed together. Thus, the asymmetric alkyl compound was synthesized, as in Example 1. Results are shown in Table 12 below.

moisture in the wet state alkali-treated solid support was 12%, the length of time necessary for completing the asymmetric alkylation was 0.08 hour, that is, the length of time was reduced so as to be about one sixth of the length of time when using the dried alkali-treated solid support (see the third and fifth lines in Table 12).

Further, when (i) used as the solvent was a mixed solvent of toluene and trichloromethane (5:5) and (ii) the ratio of the moisture in the wet state alkali-treated solid support was from 0.6% to 16%, the length of time necessary for completing the asymmetric alkylation was from 0.033 hour to 0.5 hour, that is, the length of time was reduced significantly as compared with the length of time when using the dried alkali-treated solid support (see the sixth and fifteenth lines in Table 12). Especially, when the ratio of the moisture in the wet state alkali-treated solid support was from 4.3% to 14%, the length of time necessary for completing the asymmetric alkylation was from 0.033 hour to 0.25 hour, that is, the length of time

TABLE 12

| | Amount of Moisture (%) | Solvent | Time (h) | Yield (%) | Enantiomer Excess (%) | Absolute Configuration |
|---|---|---|---|---|---|---|
| 1 | 0 | $CH_2Cl_2$ | 0.5 | 97 | 82 | S |
| 2 | 12 | $CH_2Cl_2$ | 0.5 | 91 | 86 | S |
| 3 | 0 | $PhCH_3$—$CH_2Cl_2$ (3:7) | 0.5 | 95 | 80 | S |
| 4 | 2.1 | $PhCH_3$—$CH_2Cl_2$ (5:5) | 0.5 | 91 | 86 | S |
| 5 | 12 | $PhCH_3$—$CH_2Cl_2$ (3:7) | 0.08 | 89 | 83 | S |
| 6 | 0 | $PhCH_3$—$CHCl_3$ (5:5) | 2.0 | 89 | 91 | S |
| 7 | 0.6 | $PhCH_3$—$CHCl_3$ (5:5) | 0.5 | 91 | 84 | S |
| 8 | 2.1 | $PhCH_3$—$CHCl_3$ (5:5) | 0.33 | 93 | 89 | S |
| 9 | 2.1 | $PhCH_3$—$CHCl_3$ (5:5) | 0.5 | 91 | 89 | S |
| 10 | 4.3 | $PhCH_3$—$CHCl_3$ (5:5) | 0.25 | 87 | 89 | S |
| 11 | 6.8 | $PhCH_3$—$CHCl_3$ (5:5) | 0.033 | 89 | 88 | S |
| 12 | 9.6 | $PhCH_3$—$CHCl_3$ (5:5) | 0.033 | 91 | 80 | S |
| 13 | 12 | $PhCH_3$—$CHCl_3$ (5:5) | 0.12 | 90 | 84 | S |
| 14 | 14 | $PhCH_3$—$CHCl_3$ (5:5) | 0.17 | 89 | 87 | S |
| 15 | 16 | $PhCH_3$—$CHCl_3$ (5:5) | 0.33 | 87 | 89 | S |
| 16 | 18 | $PhCH_3$—$CHCl_3$ (5:5) | 4.0 | 85 | 88 | S |

Here, each of the fourth and ninth lines in Table 12 shows a result when the reaction solution was prepared using 2 mol % of the asymmetric catalyst. Moreover, each of the first to third, fifth to eighth, and tenth to sixteenth lines in Table 12 shows a result when the reaction solution was prepared using 10 mol % of the asymmetric catalyst.

As shown in Table 12, in Example 12, the asymmetric alkylation was carried out using (i) three different solvents (which were different in blend ratio or kind) and (ii) different alkali-treated solid supports (which were different in the ratio of the moisture), and a product was obtained under each condition. As a result, a length of time necessary for completing the asymmetric alkylation was from 0.033 hour to 4 hours. Further, the yield of the product was from 85% to 97%, and the enantiomer excess was from 80% to 91%. Moreover, when used as the solvent was dichloromethane, the length of time necessary for completing the asymmetric alkylation, the yield of the product, and the enantiomer excess were substantially the same between when the wet state alkali-treated solid support (the rate of the moisture was 12%) was used and when the dried alkali-treated solid support was used. Moreover, when (i) used as the solvent was a mixed solvent of toluene ($PhCH_3$) and dichloromethane (3:7) or a mixed solvent of toluene and dichloromethane (5:5) and (ii) the ratio of the was reduced further significantly as compared with the length of time when using the dried alkali-treated solid support (see the tenth and fourteenth lines in Table 12). Especially, when the ratio of the moisture in the wet state alkali-treated solid support was 6.8% or 9.6%, the length of time necessary for completing the asymmetric alkylation was 0.033 hour, that is, the length of time was reduced so as to be about one sixtieth of the length of time when using the dried alkali-treated solid support.

Moreover, as shown in the fourth or ninth line in Table 12, even when the reaction solution was prepared using 2 mol % of the asymmetric catalyst, the length of time necessary for completing the asymmetric alkylation was 0.5 hour, that is, the length of time was substantially equal to the length of time when the reaction solution was prepared using 10 mol % of the asymmetric catalyst.

These results show that, as compared with a case in which the moisture of the alkali-treated solid support was completely removed, the reaction rate of the asymmetric alkylation was significantly increased by removing the moisture of the alkali-treated solid support so that the rate of the moisture in the alkali-treated solid support can be from 0.6% to 16%. Further, these results also show that, by removing some moisture in the alkali-treated solid support, the amount of asymmetric catalyst used can be reduced, and the asymmetric alkylation can be carried out using this small amount of asymmetric catalyst.

EXAMPLE 13

Example 13 used a reaction solution prepared by dissolving 2 mol % (0.001 mmol) of an asymmetric catalyst, 0.05 mmol of a glycine imine ester, and 0.084 mmol of an alkyl halide in a solvent. Here, used as the glycine imine ester was an N-dimethylmethylene glycine-t-butyl ester, used as the alkyl halide was a 2-(bromomethyl) benzene, and used as the asymmetric catalyst was S,S-NASB. Moreover, used as the solvent was a mixed solvent of toluene ($PhCH_3$) and dichloromethane (7:3) or a mixed solvent of toluene and dichloromethane (5:5).

Moreover, used as the alkali-treated solid support was kaolin/KOH. The wet state alkali-treated solid support was prepared by using the same method as in Example 11. In Example 13, a length of time necessary for removing the moisture in the wet state alkali-treated solid support with a rotary evaporator in a reduced pressure environment was suitably set so that the ratio of the moisture in the wet state alkali-treated solid support can be from 0% to 18%. 0.51 gram of the alkali-treated solid support was added to the reaction solution, and these were mixed together. Thus, the asymmetric alkyl compound was synthesized, as in Example 1. Results are shown in Table 13 below.

TABLE 13

| | Amount of Moisture (%) | Solvent | Time (h) | Yield (%) | Enantiomer Excess (%) | Absolute Configuration |
|---|---|---|---|---|---|---|
| 1 | 0 | $PhCH_3$—$CH_2Cl_2$ (7:3) | 6.0 | 91 | 86 | R |
| 2 | 2.1 | $PhCH_3$—$CH_2Cl_2$ (7:3) | 0.50 | 90 | 86 | R |
| 3 | 12 | $PhCH_3$—$CH_2Cl_2$ (7:3) | 0.17 | 90 | 94 | R |
| 4 | 18 | $PhCH_3$—$CHCl_3$ (5:5) | 0.50 | 91 | 89 | R |

As shown in Table 13, in Example 13, used as the asymmetric catalyst was S,S-NASB. Further, in Example 13, the asymmetric alkylation was carried out using different alkali-treated solid supports (which were different in the amount of the moisture and/or the kind of the solvent), and a product was obtained under each condition. As a result, a length of time necessary for completing the asymmetric alkylation was from 0.17 hour to 6 hours. Further, the yield of the product was from 90% to 91%, and the enantiomer excess was from 86% to 94%. Further, even when the asymmetric alkylation was carried out using the wet state alkali-treated solid support, the length of time necessary for completing the asymmetric alkylation was 0.5 hour or 0.17 hour, that is, the length of time was reduced significantly as compared with the length of time when using the dried alkali-treated solid support.

Moreover, according to the results shown in Table 13, the major (excessive) optical isomer contained in each of the products obtained under four different conditions was the (R) body.

These results show that, as the asymmetric catalyst, S,S-NASB has the same performance (the yield of the product, and the enantiomer excess) as HCD-allyl.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

An asymmetric alkyl compound producing method of the present invention can be used for producing an asymmetric alkyl compound, etc. The asymmetric alkyl compound may be, for example, a highly optically pure amino acid precursor. Therefore, the present invention can be utilized in various industries, such as a pharmaceutical industry, a food industry, an agricultural industry, etc.

The invention claimed is:

1. A method for producing an asymmetric alkylated glycine imine ester by an asymmetric synthesis reaction between a glycine imine ester and an alkyl halide, comprising:
a synthesizing step of carrying out the asymmetric synthesis reaction by mixing (i) a reaction solution containing the glycine imine ester, the alkyl halide, and an asymmetric catalyst having a catalytic action which causes the asymmetric synthesis reaction to proceed with (ii) an alkali-treated solid support obtained by treating with an alkaline substance a solid support made of an inorganic compound wherein the glycine imine ester has a structure shown by Formula (6) below, $$(R^1)_2C=N—CH_2—COO—R^2 \qquad (6)$$

where each of R1 and $R^2$ denotes a monovalent organic group.

2. The method as set forth in claim 1, wherein said mixing is carried out so that the reaction solution is formed as a thin film on a surface of the alkali-treated solid support.

3. The method as set forth in claim 1, wherein said mixing is carried out by dropping the reaction solution onto the alkali-treated solid support.

4. The method as set forth in claim 1, wherein the alkali-treated solid support is a powder.

5. The method as set forth in claim 1, wherein after said mixing, a mixture of the reaction solution and the alkali-treated solid support is dried and then is subjected to a microwave irradiation treatment.

6. The method as set forth in claim 1, wherein the solid support is any one of a clay mineral and an inorganic oxide.

7. The method as set forth in claim 6, wherein the inorganic oxide is any one of a metal oxide and a silicone oxide.

8. The method as set forth in claim 1, wherein the solid support is any one selected from a group consisting of alumina, kaolin, kaolinite, montmorillonite, bentonite, celite, zeolite, and diatomous earth.

9. The method as set forth in claim 1, wherein used as the alkaline substance for treating the solid support is an aqueous solution of an alkali compound.

10. The method as set forth in claim 9, wherein used as the alkali compound is a hydroxide of alkali metal or a hydroxide of alkaline earth metal.

11. The method as set forth in claim 9, wherein the alkali-treated solid support is obtained by a preparation method including (i) a treating step of treating the solid support with the aqueous solution of the alkali compound, and (ii) a drying step of drying the solid support thus treated.

12. The method as set forth in claim 11, wherein in said drying step, the treated solid support is subjected to a microwave irradiation treatment so as to be dried.

13. The method as set forth in claim 9, wherein the alkali-treated solid support is obtained by a preparation method including (i) a treating step of treating the solid support with the aqueous solution of the alkali compound, and (ii) a wet-state step of changing the treated solid support into a wet state.

14. The method as set forth in claim 13, wherein in said wet-state step, moisture in the treated solid support is removed so that the amount of the moisture is in a range from 0.1% by weight to 50% by weight.

15. The method as set forth in claim 1, wherein the asymmetric catalyst is a cinchonidine-based compound or a cinchonine-based compound.

16. The method as set forth in claim 1, wherein the asymmetric catalyst is cinchonine or an N-anthracenyl methyl cinchonidium chloride.

17. The method as set forth in claim 1, wherein the asymmetric catalyst is an N-spiro quaternary ammonium salt.

18. The method as set forth in claim 1, wherein the organic group denoted by $R^1$ in Formula (6) is an alkyl group having an aromatic structure.

19. The method as set forth in claim 18, wherein the organic group denoted by $R^2$ in Formula (6) includes a side chain having three or more carbons.

20. The method as set forth in claim 19, wherein the organic group denoted by $R^2$ is a t-butyl group (a methyl propyl group).

21. The method as set forth in claim 1, wherein the glycine imine ester is an N-dimethylphenylmethylene glycine t-butyl ester.

22. The method as set forth in claim 1, wherein the alkyl halide has a structure shown by Formula (7) below, $$R^3-X \qquad (7)$$

where $R^3$ denotes a monovalent organic group, and X denotes a halogen atom.

23. The method as set forth in claim 22, wherein the halogen is bromine (Br), iodine (I) or chlorine (Cl).

24. The method as set forth in claim 22, wherein the organic group denoted by $R^3$ is an alkyl group.

* * * * *